(12) United States Patent
Goredema et al.

(10) Patent No.: US 8,101,801 B2
(45) Date of Patent: Jan. 24, 2012

(54) LOW MOLECULAR WEIGHT QUATERNARY AMMONIUM SALT DISPERSANTS

(75) Inventors: Adela Goredema, Mississauga (CA); Aaron Strong, Hamilton (CA); Peter Odell, Mississauga (CA); C. Geoffrey Allen, Waterdown (CA); Mihaela Maria Birau, Mississauga (CA)

(73) Assignee: Xerox Corporation, Norwalk, CT (US)

(*) Notice: Subject to any disclaimer, the term of this patent is extended or adjusted under 35 U.S.C. 154(b) by 174 days.

(21) Appl. No.: 12/467,692

(22) Filed: May 18, 2009

(65) Prior Publication Data

US 2010/0292467 A1  Nov. 18, 2010

(51) Int. Cl.
*C07C 321/04* (2006.01)
(52) U.S. Cl. .................................................. 564/192
(58) Field of Classification Search .................. 564/192
See application file for complete search history.

(56) References Cited

U.S. PATENT DOCUMENTS

| | | |
|---|---|---|
| 2,562,383 A | 7/1951 | Kautenberg |
| 3,113,026 A | 12/1963 | Sprung |
| 3,945,836 A | 3/1976 | Miyata |
| 4,046,873 A | 9/1977 | Bauman |
| 4,251,824 A | 2/1981 | Hara et al. |
| 4,342,706 A | 8/1982 | Conner et al. |
| 4,410,899 A | 10/1983 | Haruta et al. |
| 4,412,224 A | 10/1983 | Sugitani |
| 4,490,731 A | 12/1984 | Vaught |
| 4,532,530 A | 7/1985 | Hawkins |
| 4,601,777 A | 7/1986 | Hawkins et al. |
| 4,830,671 A | 5/1989 | Frihart et al. |
| 4,889,560 A | 12/1989 | Jaeger et al. |
| 4,889,761 A | 12/1989 | Titterington et al. |
| 5,053,079 A | 10/1991 | Haxell et al. |
| 5,194,638 A | 3/1993 | Frihart et al. |
| 5,220,346 A | 6/1993 | Carreira et al. |
| 5,221,335 A | 6/1993 | Williams et al. |
| 5,372,852 A | 12/1994 | Titterington et al. |
| 5,597,856 A | 1/1997 | Yu et al. |
| 5,750,604 A | 5/1998 | Banning et al. |
| 5,780,528 A | 7/1998 | Titterington et al. |
| 5,782,966 A | 7/1998 | Bui et al. |
| 5,783,658 A | 7/1998 | Banning et al. |
| 5,827,918 A | 10/1998 | Titterington et al. |
| 5,830,942 A | 11/1998 | King et al. |
| 5,919,839 A | 7/1999 | Titterington et al. |
| 6,001,160 A | 12/1999 | Jaeger et al. |
| 6,001,901 A | 12/1999 | Shiobara et al. |
| 6,086,661 A | 7/2000 | Malhotra et al. |
| 6,106,602 A | 8/2000 | Ouchi et al. |
| 6,174,937 B1 | 1/2001 | Banning et al. |
| 6,176,911 B1 | 1/2001 | Schwarz |
| 6,200,369 B1 | 3/2001 | Schwarz |
| 6,255,432 B1 | 7/2001 | Evans et al. |
| 6,309,453 B1 | 10/2001 | Banning et al. |
| 6,372,934 B1 | 4/2002 | O'Lenick |
| 6,547,380 B2 | 4/2003 | Smith et al. |
| 6,858,070 B1 | 2/2005 | Wong et al. |
| 6,860,930 B2 | 3/2005 | Wu et al. |
| 6,906,118 B2 | 6/2005 | Goodbrand et al. |
| 2003/0127021 A1 | 7/2003 | Brown |
| 2003/0130374 A1 | 7/2003 | Smith et al. |
| 2004/0261656 A1 | 12/2004 | Wu et al. |
| 2005/0090423 A1 | 4/2005 | Ushio et al. |
| 2008/0098927 A1 | 5/2008 | Allen et al. |
| 2008/0098929 A1 | 5/2008 | Turek et al. |

FOREIGN PATENT DOCUMENTS

| | | |
|---|---|---|
| DE | 199 34 281 A1 | 1/2001 |
| DE | 103 09 180 A1 | 6/2004 |
| EP | 0 522 157 A1 | 1/1993 |
| EP | 535973 | 4/1993 |
| EP | 535974 | 4/1993 |
| EP | 1 698 726 A1 | 9/2006 |
| GB | 777488 | 6/1957 |
| GB | 2 177 720 A | 1/1987 |
| GB | 2 238 792 | 6/1991 |
| GB | 2 290 793 | 1/1996 |
| GB | 2 294 939 | 5/1996 |
| GB | 2 305 670 | 4/1997 |
| GB | 2 305 928 | 4/1997 |
| GB | 2 433 264 A | 6/2007 |
| JP | A-61-293886 | 12/1986 |
| JP | A-2000-280462 | 10/2000 |
| JP | A-2000-351273 | 12/2000 |
| JP | A-2003-292692 | 10/2003 |
| JP | 2005-343859 | 12/2005 |
| JP | 2008-088130 | 4/2008 |
| WO | 91/11983 | 8/1991 |
| WO | 94/14902 | 7/1994 |
| WO | 95/04760 | 2/1995 |
| WO | 96/14364 | 5/1996 |
| WO | 97/12003 | 4/1997 |

(Continued)

OTHER PUBLICATIONS

Aug. 16, 2010 European Search Report issued in EP 10 16 2554.

(Continued)

*Primary Examiner* — Rebecca Anderson
(74) *Attorney, Agent, or Firm* — Oliff & Berridge, PLC

(57) ABSTRACT

Disclosed is a chemical compound having the structure:

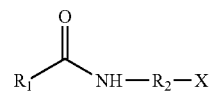

wherein $R_1$ is an all group, aryl group, alkylaryl group or arylalkyl group with at least 23 carbon atoms, $R_2$ is an alkylene group, arylene group, alkyarylene group or arylalkylene group with at least 2 carbons and X is a quaternary ammonium salt.

4 Claims, 3 Drawing Sheets

FOREIGN PATENT DOCUMENTS

| WO | 97/13816 | 4/1997 |
| WO | WO 97/12020 | 4/1997 |
| WO | WO 97/18273 | 5/1997 |
| WO | 97/33943 | 9/1997 |
| WO | 99/42523 | 8/1999 |
| WO | WO 2008/133809 A1 | 11/2008 |
| WO | WO 2009/093872 A2 | 7/2009 |

OTHER PUBLICATIONS

Database Caplus [Online] Chemical Abstracts Service, 2000, Imaeda, M. "Ink-jet ink pellets free from possible swallowing and suffocation by babies and infants" XP002594294 retrieved from STN Database accession No. 2000:715390.

Sep. 13, 2010 European Search Report issued in EP 10 16 2505.

Jul. 14, 2011 Office Action issued in U.S. Appl. No. 12/467,769.

LOW MOLECULAR WEIGHT QUATERNARY AMMONIUM SALT DISPERSANTS

RELATED APPLICATIONS

Commonly assigned U.S. patent application Ser. No. 12/467,769, entitled "Pigmented Phase Change Inks Containing Low Molecular Weight Quaternary Ammonium Salt Dispersants"), filed concurrently herewith, describes phase change inks wherein a dispersant compound, used to stabilize pigment particles, includes a long hydrophobic chain and a quaternary ammonium salt.

Commonly assigned U.S. Patent Application Publication No. 20080098927A1, filed Oct. 26, 2006, describes a phase change ink comprising an ink vehicle, at least one colorant and at least one dispersant, wherein the dispersant comprises first functional groups that anchor the dispersant to the pigment particles and second functional groups that are compatible with the ink vehicle.

Commonly assigned U.S. Patent Application Publication No. 20080098929A1, filed Oct. 26, 2006, describes a phase change ink comprising an ink vehicle, at least one colorant and at least one dispersant, wherein the at least one dispersant comprises at least one triamide, and at least one bis-urethane and/or at least one carbamate resin.

The appropriate components and process aspects of the foregoing, such as the dispersant materials, may be selected for the present disclosure in embodiments thereof. The entire disclosure of the above-mentioned application is totally incorporated herein by reference.

TECHNICAL FIELD

Described herein are inks such as solid phase change or hot melt inks that may be used in a number of copying and printing devices. More particularly, described herein are compounds that may be used as dispersants for the pigment particles in such inks, methods of making such compounds, and inks containing these compounds.

BACKGROUND

Ink jetting devices are well known in the art. As described in U.S. Pat. No. 6,547,380, ink jet printing systems are generally of two types: continuous stream and drop-on-demand. In continuous stream ink jet systems, ink is emitted in a continuous stream under pressure through at least one orifice or nozzle. The stream is perturbed, causing it to break up into droplets at a fixed distance from the orifice. At the break-up point, the droplets are charged in accordance with digital data signals and passed through an electrostatic field that adjusts the trajectory of each droplet in order to direct it to a gutter for recirculation or a specific location on a recording medium. In drop-on-demand systems, a droplet is expelled from an orifice directly to a position on a recording medium in accordance with digital data signals. A droplet is not formed or expelled unless it is to be placed on the recording medium. There are generally three types of drop-on-demand ink jet systems. One type of drop-on-demand system is a piezoelectric device that has as its major components an ink filled channel or passageway having a nozzle on one end and a piezoelectric transducer near the other end to produce pressure pulses. Another type of drop-on-demand system is known as acoustic ink printing. As is known, an acoustic beam exerts a radiation pressure against objects upon which it impinges. Thus, when an acoustic beam impinges on a free surface (i.e., liquid/air interface) of a pool of liquid from beneath, the radiation pressure which it exerts against the surface of the pool may reach a sufficiently high level to release individual droplets of liquid from the pool, despite the restraining force of surface tension. Focusing the beam on or near the surface of the pool intensifies the radiation pressure it exerts for a given amount of input power. Still another type of drop-on-demand system is known as thermal ink jet, or bubble jet, and produces high velocity droplets. The major components of this type of drop-on-demand system are an ink filled channel having a nozzle on one end and a heat generating resistor near the nozzle. Printing signals representing digital information originate an electric current pulse in a resistive layer within each ink passageway near the orifice or nozzle, causing the ink vehicle (usually water) in the immediate vicinity to vaporize almost instantaneously and create a bubble. The ink at the orifice is forced out as a propelled droplet as the bubble expands.

In a typical design of a piezoelectric ink jet device, the image is applied by jetting appropriately colored inks during four to eighteen rotations (incremental movements) of a substrate such as an image receiving member or intermediate transfer member with respect to the ink jetting head, i.e., there is a small translation of the printhead with respect to the substrate in between each rotation. This approach simplifies the printhead design, and the small movements ensure good droplet registration. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops.

Thermal ink jet processes are well known and are described, for example, in U.S. Pat. Nos. 4,601,777, 4,251,824, 4,410,899, 4,412,224 and 4,532,530.

Ink jet printing processes may employ inks that are solid at room temperature and liquid at elevated temperatures. Such inks may be referred to as hot melt inks or phase change inks. For example, U.S. Pat. No. 4,490,731 discloses an apparatus for dispensing solid ink for printing on a substrate such as paper. In thermal ink jet printing processes employing hot melt inks, the solid ink is melted by the heater in the printing apparatus and utilized (i.e., jetted) as a liquid in a manner similar to that of conventional thermal ink jet printing. Upon contact with the printing substrate, the molten ink solidifies rapidly, enabling the colorant to substantially remain on the surface of the substrate instead of being carried into the substrate (for example, paper) by capillary action, thereby enabling higher print density than is generally obtained with liquid inks. Advantages of a phase change ink in ink jet printing are thus elimination of potential spillage of the ink during handling, a wide range of print density and quality, minimal paper cockle or distortion, and enablement of indefinite periods of nonprinting without the danger of nozzle clogging, even without capping the nozzles.

Pigmented phase change ink compositions that include various dispersants are also known. For example, pigmented phase change ink compositions that include SOLSPERSE™ dispersants are described in WO 99/42523 and U.S. Patent Publication No. 2003/0127021. Exemplary patents that disclose pigmented phase change ink compositions using other dispersants include U.S. Pat. Nos. 5,053,079, 5,221,335, and 6,001,901 and European Patent publications 535973 and 535974.

However, the use of polymeric and oligomeric dispersants is not favored in some phase change inks for a variety of reasons. The problems caused by the use of polymeric or oligomeric dispersants include a negative effect on Theological properties of the ink, such as non-Newtonian behavior and an increase in viscosity. Polymeric and oligomeric dispersants in phase change inks also affect drop formation, because polymers will tend to form filaments which affect the formation of small drop sizes.

The disclosures of each of the foregoing patents and publications are hereby incorporated by reference herein in their entireties. The appropriate components and process aspects of the each of the foregoing patents and publications may also be selected for the present compositions and processes in embodiments thereof.

While known compositions and processes are suitable for their intended purposes, a need remains for an improved colored phase change ink composition. For example, there remains a need for phase change inks with pigment colorants where the pigment particles are stable and well dispersed in the ink. There remains a need for pigmented phase change inks with improved image quality, improved light fastness, and reduced show through. A need also remains for pigmented phase change inks where the colorants have reduced agglomeration and settling in the ink when the ink is exposed to high temperatures for prolonged periods. A need also remains for pigmented phase change inks with reduced clogging of the jets in the printhead.

SUMMARY

The present disclosure addresses these and other needs, by providing improved pigmented phase change inks containing low molecular weight quaternary ammonium salt dispersants, novel compounds that can act as such dispersants, and methods of making these compounds.

In embodiments, this disclosure provides dispersant compounds having a general formula:

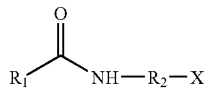

wherein $R_1$ and $R_2$ are as defined below, and X is a quaternary ammonium salt.

In other embodiments, this disclosure provides a method of forming the above dispersant compound, the method including: (1) melting a carboxylic acid, under an inert atmosphere; (2) reacting a compound having a primary amine group and a tertiary amine group with the melted carboxylic acid, under an inert atmosphere and at an elevated temperature of between about 170 to about 200° C., to form a precursor amide compound; (3) cooling the precursor amide compound; (4) dissolving the precursor amide compound in an organic solvent, under an inert atmosphere; (5) reacting either dimethyl sulfate or methyl p-toluene sulfonate with the dissolved precursor amide at an elevated temperature of between about 90 to about 120° C. to form the desired compound, in the non-polar solvent and under an inert atmosphere; and (6) separating and isolating the dispersant compound.

In another embodiment, this disclosure provides a second method of forming the above dispersant compound, the method including: (1) melting a carboxylic acid, under an inert atmosphere; (2) reacting a compound having a primary amine group and a tertiary amine group with the melted carboxylic acid, under an inert atmosphere and at an elevated temperature of between about 170 to about 200° C. to form a precursor amide compound; (3) lowering the temperature to a range of about 130 to about 160° C.; (4) reacting either dimethyl sulphate or methyl p-toluene sulfonate with the precursor amide compound at an elevated temperature of between about 130 to about 160° C. under an inert atmosphere; and (5) separating and isolating the dispersant compound.

In still another embodiment, this disclosure provides an ink comprising an ink vehicle, pigment particles, and a dispersant; where the dispersant is the dispersant compound described above.

EMBODIMENTS

Figure 1:
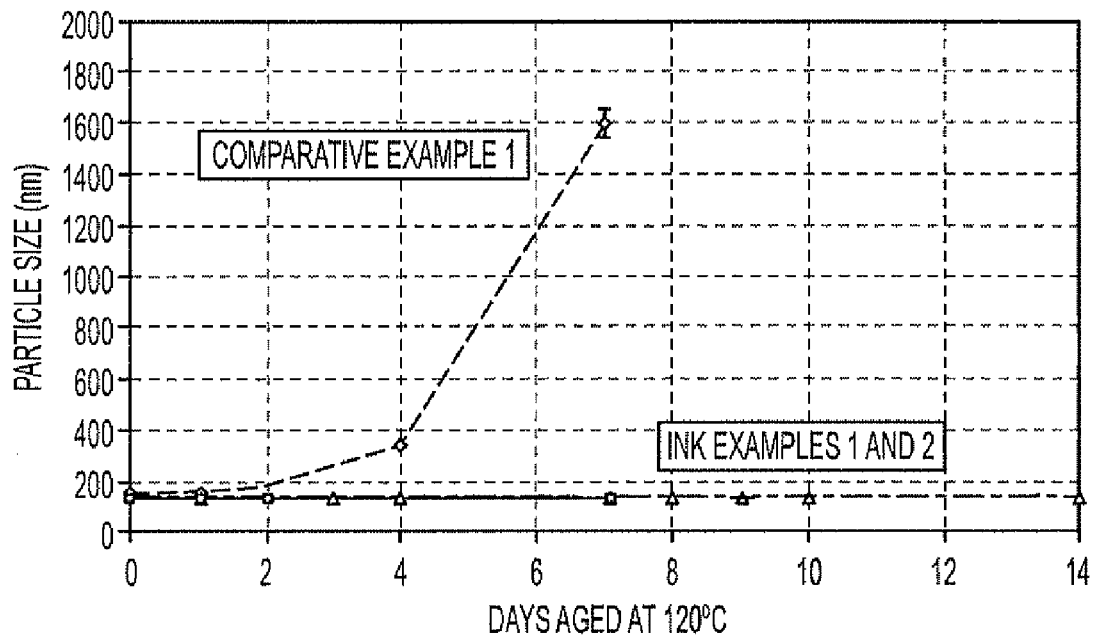
FIG. 1 shows pigment Z-average particle sizes over time of phase change ink examples 1 and 2 comprising dispersant example 3 compared to comparative ink example 1.

This disclosure is not limited to particular embodiments described herein, and some components and processes may be varied by one of ordinary skill in the art, based on this disclosure. The terminology used herein is for the purpose of described particular embodiments only, and is not intended to be limiting.

The Dispersant Compound

Chemical compounds having the following formula may be used as a dispersant in a phase change ink. Generally, the compounds can be represented by the formula:

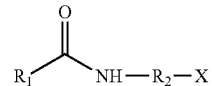

wherein $R_1$ is
(i) an alkyl group, which may be linear or branched, cyclic or acyclic, substituted or unsubstituted, and wherein hetero atoms such as oxygen, nitrogen, sulfur, silicon, phosphorus and the like either may or may not be present in the alkyl group, in one embodiment with at least about 1 carbon atom, in another embodiment with at least about 16 carbon atoms, and in yet another embodiment with at least about 23 carbon atoms, and in one embodiment with no more than about 200 carbon atoms, in another embodiment with no more than about 150 carbon atoms, and in yet another embodiment with no more than about 100 carbon atoms, although the number of carbon atoms can be outside of these ranges,
(ii) an arylalkyl group, which may be substituted or unsubstituted, wherein the alkyl portion of the arylalkyl group can be linear or branched, cyclic or acyclic, substituted or unsubstituted, and wherein hetero atoms such as oxygen, nitrogen, sulfur, silicon, phosphorus and the like either may or may not be present in either the aryl or the alkyl portion of the arylalkyl group, in one embodiment with at least about 6 carbon atoms, and in another embodiment with at least about 23 carbon atoms, and in one embodiment with no more than about 200 carbon atoms, in another embodiment with no more than about 150 carbon atoms, and in yet another embodiment with no more than about 100 carbon atoms, although the number of carbon atoms can be outside of these ranges; or (iii) an alkylaryl group, which may be substituted or unsubstituted, wherein the alkyl portion of the alkylaryl group can be linear or branched, cyclic or acyclic, substituted or unsubstituted, and wherein hetero atoms such as oxygen, nitrogen, sulfur, silicon, phosphorus and the like either may or may not be present in either the aryl or the alkyl portion of the alkylaryl group, in one embodiment with at least about 6 carbon atoms, and in another embodiment with at least about 23 carbon atoms, and in one embodiment with no more than about 200 carbon atoms, in another embodiment with no more than about 150 carbon atoms, and in yet another embodiment with no more than about 100 carbon atoms, although the number of carbon atoms can be outside of these ranges, $R_2$ is (i) alkylene group, which may be linear or branched, saturated or unsaturated, cyclic or acyclic, substituted or unsubstituted, and wherein hetero atoms as oxygen, nitrogen, sulfur, silicon, phosphorus and the like either may or may not be present in the alkylene group, in one embodiment with at least about 1 carbon atom, and in another embodiment with at least about 2 carbon atoms, and in one embodiment with no more than about 20 carbon atoms, in another embodiment with no more than about 10 carbon atoms, and in yet another embodiment with no more than about 8 carbon atoms, although the number of carbon atoms can be outside of these ranges, (ii) arylene groups, which may be substituted or unsubstituted, and wherein hetero atoms either may or may not be present in the arylene group, in one embodiment with at least about 6 carbon atoms, and in another embodiment with at least about 7 carbon atoms, and in one embodiment with no more than about 20 carbon atoms, in another embodiment with no more than about 15 carbon atoms, and in yet another embodiment with no more than about 10 carbon atoms, although the number of carbon atoms can be outside of these ranges, (iii) arylalkylene groups, which may be substituted or unsubstituted, wherein the alkyl portion of the arylalkylene group can be linear or branched, saturated or unsaturated, cyclic or acyclic, substituted or unsubstituted, and wherein hetero atoms as oxygen, nitrogen, sulfur, silicon, phosphorus and the like either may or may not be present in either the aryl or the alkyl portion of the arylalkylene group, in one embodiment with at least about 7 carbon atoms, and in another embodiment with at least about 8 carbon atoms, and in one embodiment with no more than about 20 carbon atoms, in another embodiment with no more than about 15 carbon atoms, and in yet another embodiment with no more than about 10 carbon atoms, although the number of carbon atoms can be outside of these ranges, or (iv) alkylarylene groups, which may be substituted or unsubstituted, wherein the alkyl portion of the alkylarylene group can be linear or branched, saturated or unsaturated, cyclic or acyclic, substituted or unsubstituted, and wherein hetero atoms as oxygen, nitrogen, sulfur, silicon, phosphorus and the like either may or may not be present in either the aryl or the alkyl portion of the alkylarylene group, in one embodiment with at least about 7 carbon atoms, and in another embodiment with at least about 8 carbon atoms, and in one embodiment with no more than about 20 carbon atoms, in another embodiment with no more than about 15 carbon atoms, and in yet another embodiment with no more than about 10 carbon atoms, although the number of carbon atoms can be outside of these ranges, and X is a quaternary ammonium salt.

In particular embodiments, $R_1$ can be a linear alkyl chain of formula $CH_3(CH_2)n\text{-}$. In one specific embodiment n has an average value of 28 carbons and has a range of from about 20 to about 40, in another specific embodiment n has an average value of 36 and has a range of from about 34 to about 40, in yet another specific embodiment n has an average value of 46 and has a range of from about 40 to about 52.

The group $R_2$ between the amide group and the quaternary ammonium salt group can generally be any alkylene, arylene, etc. Generally, an alkylene or arylene group refers to a secondary carbon atom, i.e. one with two substituents. In embodiments, $R_2$ can be a linear alkylene group having between 2 and 4 carbon atoms. For example, $R_2$ may be a linear alkylene group of 2, 3, or 4 carbon atoms. Generally, the length of the $R_2$ group is determined by the nature of the precursor compound that is reacted with the carboxylic acid, as is described below. In one specific embodiment, $R_2$ is of formula $-CH_2CH_2CH_2-$.

The quaternary ammonium salt group "X" can generally be any quaternary ammonium functional group ionically bonded to a salt ion. The "X" group is generally referred to as "the anchor" of the dispersant compound. In embodiments, the quaternary ammonium salt can be any of the following salt groups:

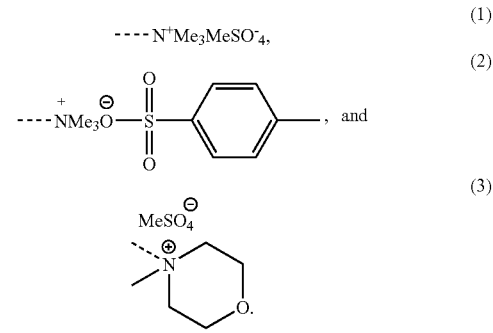

Methods for Making the Dispersant Compounds

The above discussed dispersant compounds can be synthesized according to two general reaction processes. A first reaction process is a "two pot" reaction process, whereby an intermediate is formed and then isolated before further reaction steps. A second reaction process is a "one pot" reaction process, whereby all of the reaction steps occur without isolation of an intermediate.

The first reaction process, herein referred to as the "two pot process," generally comprises the following six steps: (1) melting about 1 mole equivalent of a carboxylic acid of formula $CH_3(CH_2)_nCOOH$, under an inert atmosphere; (2) reacting the melted carboxylic acid with about 1 mole equivalent of a diamine of formula,

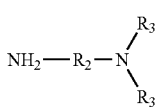

wherein $R_3$ is described below, under an inert atmosphere and at an elevated temperature such as of about 170 to about 200° C., to form a precursor amide compound of formula;

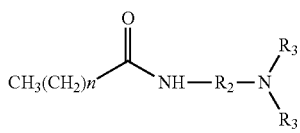

(3) cooling the precursor amide compound; (4) dissolving the precursor amide compound in an organic solvent, under an inert atmosphere; (5) reacting either about 0.85 mol equivalents dimethyl sulfate or methyl p-toluene sulfonate with about 1 mole equivalent of the dissolved precursor amide at an elevated temperature such as between about 90 to about 120° C. to form the desired compound, in the non-polar solvent and under an inert atmosphere; and (6) separating and isolating the dispersant compound. The "two pot process" proceeds as follows:

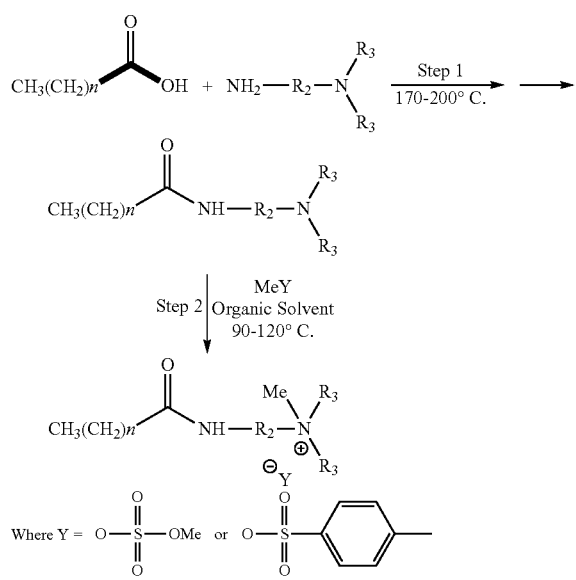

wherein MeY is the salting agent.

In embodiments, the two pot process may include additional process steps. For example, the step (2) can include the removal of water, such as through evaporation. Additionally, the step (6) of two pot process may include distillation, vacuum removal of the solvent and vacuum removal, for example, of either the residual dimethyl sulfate or methyl p-toluene sulfonate.

In embodiments, the two pot process may include any additional chemical synthesis steps according to the knowledge of a person having ordinary skill in the art. In other embodiments, the two pot process consists essentially of the above listed six steps, or consists of only the above listed six steps.

The carboxylic acid can generally be any carboxylic acid, such that the resulting compound has a linear alkyl group $R_1$ that includes at least 23 carbon atoms. The group $R_1$ in the resulting dispersant compound is formed from the carboxylic acid alkyl chain, and therefore the particular carboxylic acid is chosen based on the desired length of $R_1$. For example, the carboxylic acid may be a carboxylic acid having an alkyl chain with a number of carbon atoms as is discussed above.

The inert atmosphere can be any atmosphere that does not contain compounds that will react with the compounds in the chemical process. Inert atmospheres are generally known according to the knowledge of a person having ordinary skill in the art. For example, the inert atmosphere may be an atmosphere made up of only a noble gas, such as argon.

The diamine can generally be any diamine having these functional groups. Namely, the diamine must have at least one primary amine —$NH_2$ group, and at least one tertiary amine —$N(R_3)_2$ group. Generally, the diamine can be any compound having the general formula $NH_2$—$R_2$—$N(R_3)_2$, where $R_2$ is defined as discussed above and $R_3$ is any suitable amine substituent such (i) an alkyl group, which maybe linear or branched, cyclic or acyclic, substituted or unsubstituted, and wherein hetero atoms either may or may not be present in the alkyl group; (ii) alkylaryl group which may be substituted or unsubstituted, wherein the alkyl portion of the alkylarylene group can be linear or branched, cyclic or acyclic, substituted or unsubstituted, and wherein hetero atoms either may or may not be present in either the aryl or the alkyl portion of the alkylarylene group. In particular embodiments, the diamine can be 3-(dimethylamino)-1-propylamine, or aminopropylmorpholine.

The non-polar solvent used in step (4) can generally be any non-polar organic solvent. For example, in embodiments, the organic solvent can be toluene, dichloromethane, methyl ethyl ketone, tetrahydrofuran, or any other suitable organic solvents.

The resulting precursor amide formed by steps (1)-(4) is reacted with either of dimethyl sulfate or methyl p-tolune sulfonate to form a quaternary ammonium salt group from the tertiary amide group. For example, dimethyl sulfate or methyl p-toluene sulfonate can be suitably chosen because these compounds will form a quaternary ammonium salt group under moderate heating.

The precursor amide and the salting agent (MeY) are present in any desired or effective relative amounts, in one embodiment at least about 0.50 mole of salting agent per every 1 mole of amide precursor, in another embodiment at least about 0.65 moles of salting agent per every 1 mole of amide precursor, and in yet another embodiment at least about 0.85 moles of salting agent per every one mole of amide precursor, and in one embodiment no more than about 1 mole of salting agent per every mole of amide precursor, in another embodiment no more than about 0.98 moles of salting agent per every mole of amide precursor, and in yet another embodiment no more than about 0.95 mole of salting agent per every 1 mole of amide precursor, although the relative amounts can be outside of these ranges.

The steps of cooling and isolating in steps (3) and (6) can be performed according to the knowledge of a person having ordinary skill in the art. Various techniques for these processing steps are known in the chemical arts.

The amide precursor and the salting agent (MeY) in step 2 are present in any desired or effective relative amounts, in one embodiment at least about 0.50 moles of salting agent per every 1 mole of amide precursor, in another embodiment at least about 0.65 moles of diamine per every 1 mole of amide precursor, and in yet another embodiment at least about 0.85 moles of salting agent per every one mole of amide precursor, and in one embodiment no more than about 1 moles of salting agent per every 0.99 moles of amide precursor, in another embodiment no more than about 0.95 moles of salting agent per every mole of amide precursor, and in yet another embodiment no more than about 1 mole of salting agent per every 1 mole of amide precursor, although the relative amounts can be outside of these ranges.

The amide precursor can also be present in the isolated quaternary ammonium salt, in one embodiment the amide precursor can be present in the final product at a level of about 1 mol %, in another embodiment at about 5 mol %, and in yet another embodiment at about 15 mol %, and in one embodiment not more than about 50 mol %, and in another embodiment not more than about 35 mol %, and in yet another embodiment not more than about 25 mol %

The reaction between the carboxylic acid and the diamine in step one can carried out for any desired or effective period of time, in one embodiment at least about 1 hour, in another embodiment at least about 2 hours, and in yet another embodiment at least about 3 hrs, and in another embodiment no more than about 10 hours, although the period of time can be outside of these ranges.

The reaction between the salting agent (MeY) and the amide precursor in step 2 can be carried out for any desired or effective period of time, in one embodiment at least about 0.2 hours, in another embodiment at least about 0.5 hours, and in yet another embodiment about 1 hour, in another embodiment not more than about 5 hours, although the period can be outside these ranges.

The second reaction process, herein referred to as the "one pot process," generally comprises the following five steps: (1) melting about 1 mol equivalent of a carboxylic acid of formula $CH_3(CH_2)nCOOH$ under an inert atmosphere; (2) reacting the melted carboxylic acid with about 1 mol equivalent of a diamine of formula;

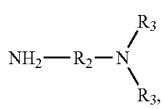

under an inert atmosphere and at an elevated temperature, such as about from 170 to about 200° C. to form a precursor amide compound of formula;

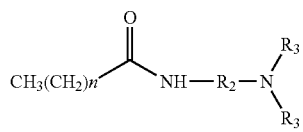

(3) lowering the temperature to, such as from about 130 to about 160° C.; (4) reacting about 0.85 mol equivalents of either dimethyl sulphate or methyl p-toluene sulfonate with the precursor amide compound at an elevated temperature, such as from about 130 to about 160° C. under an inert atmosphere; and (5) isolating the dispersant compound. Optionally increasing the temperature before the isolation of the product, such as from about 150 to about 180° C., can be considered to distill off any residual salting agent, such as dimethyl sulfate or methyl p-toluene sulfonate. The "one pot" proceeds as follows:

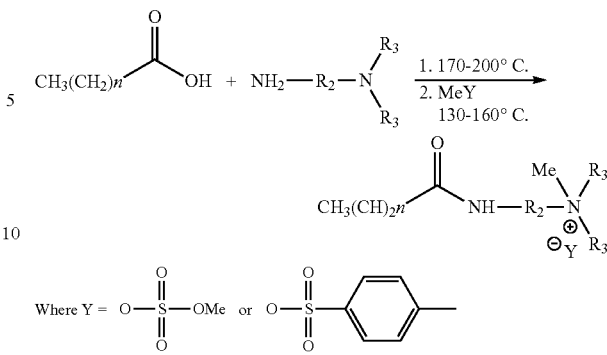

The amide precursor and the salting agent (MeY) are present in any desired or effective relative amounts, in one embodiment at least about 0.50 moles of salting agent per every 1 mole of amide precursor, in another embodiment at least about 0.65 moles of salting agent per every 1 mole of amide precursor, and in yet another embodiment at least about 0.85 moles of salting agent per every one mole of amide precursor, and in one embodiment no more than about 1 mole of salting agent per every mole of amide precursor, in another embodiment no more than about 0.98 moles of salting agent per every mole of amide precursor, and in yet another embodiment no more than about 0.95 moles of salting agent per every 1 mole of amide precursor, although the relative amounts can be outside of these ranges.

The amide precursor can also be present in the isolated quaternary ammonium salt, in one embodiment the amide precursor can be present in the final product at a level of about 1 mol %, in another embodiment at about 5 mol %, and yet another embodiment at about 15 mol %, and in one embodiment not more than about 50 mol %, and in another embodiment not more than about 35 mol %, and in yet another embodiment not more than about 25 mol %.

The reaction between the carboxylic acid and the diamine in step one can be carried in carried out for any desired or effective period of time, in one embodiment at least about 1 hour, in another embodiment at least about 2 hours, and in yet another embodiment at least about 3 hours, and in another embodiment no more than about 10 hours, although the period of time can be outside of these ranges.

The reaction between the salting agent (MeY) and the amide precursor in step 2 can be carried out for any desired or effective period of time, in one embodiment at least about 0.2 hours, in another embodiment at least about 0.5 hours, and in yet another embodiment 1 hour, in another embodiment not more than 5 hours, although the period can be outside these ranges.

In embodiments, the one pot process may include additional process steps. For example, the step (2) can include the removal of water, such as through evaporation. In other embodiments the one pot process may include a step of distillation of residual dimethyl sulphate or methyl p-toluene sulfonate In embodiments, the one pot process may include any additional chemical synthesis steps according to the knowledge of a person having ordinary skill in the art. In other embodiments, the one pot process consists essentially of the above listed five steps, or consists of only the above listed five steps. The one pot process is particularly useful when the process consists essentially of the above listed five steps, and does not include any intermediate separation step such as step (3) in the two pot process discussed above.

The Ink

The above discussed dispersant compounds can be used as dispersants in phase change inks. The phrase "used as a dispersant" means that the dispersant compound stabilizes the pigment particles in the ink vehicle by hindering the pigment particles from flocculating into larger agglomerates and thus delay settling. Generally, the dispersant compound achieves this function by adhering to the pigment particles and providing steric stabilization. The dispersant compound adheres to the pigment by, for example, being absorbed, attached or grafted to the pigment particle. In embodiments, the dispersant compound may be present in the ink in an amount of from about 0.1 to about 25 percent by weight of the ink. For example, in a particular embodiment, the dispersant compound may be present in the ink in an amount of from about 1 to about 10 percent by weight, or from about 1 to about 5 percent by weight.

Examples of the phase change inks herein are inks that include an ink vehicle that is solid at temperatures of about 23° C. to about 27° C., for example room temperature, and specifically are solid at temperatures below about 60° C. However, the inks change phase upon heating, and are in a molten state at jetting temperatures. Thus, the inks have a viscosity of from about 1 to about 20 centipoise (cP), for example from about 5 to about 15 cP or from about 8 to about 12 cP, at an elevated temperature suitable for ink jet printing, for example temperatures of from about 60° C. to about 150° C.

In this regard, the inks herein may be either low energy inks or high energy inks. Low energy inks are solid at a temperature below about 40° C. and have a viscosity of from about 1 to about 20 cP such as from about 5 to about 15 cP, for example from about 8 to about 12 cP, at a jetting temperature of from about 60 to about 125° C. such as from about 80 to about 125° C., for example from about 100 to about 120° C. High energy inks are solid at a temperature below 40° C. and have a viscosity of from about 5 to about 15 cP at a jetting temperature of from about 100 to about 180° C., for example from about 120 to about 160° C. or from about 125 to about 150° C.

Ink Vehicle

The term "ink vehicle" generally refers to the material which carries the dispersant coated pigment particles. Any suitable ink vehicle can be employed, so long as the ink vehicle is non-aqueous. For example, the ink vehicle can be a wax or a non-polar solvent. Suitable vehicles can include paraffins, microcrystalline waxes, polyethylene waxes, ester waxes, amides, long chain acids with at least about 30 carbons, fatty acids and other waxy materials, fatty amide containing materials, sulfonamide materials, resinous materials made from different natural sources (tall oil rosins and rosin esters, for example), and many synthetic resins, oligomers, polymers, and copolymers such as those further discussed below.

Examples of suitable amides include, for example, diamides, triamides, tetra-amides, cyclic amides and the like. Suitable triamides include, for example, those disclosed in U.S. Patent Publication No. 2004-0261656, the entire disclosure of which is incorporated herein by reference. Suitable other amides, such as fatty amides including monoamides, tetra-amides, and mixtures thereof, are disclosed in, for example, U.S. Pat. Nos. 4,889,560, 4,889,761, 5,194,638, 4,830,671, 6,174,937, 5,372,852, 5,597,856, and 6,174,937, and British Patent No. GB 2 238 792, the entire disclosures of each of which are incorporated herein by reference.

Other suitable vehicle materials that can be used in the solid ink compositions include, for example, isocyanate-derived resins and waxes, such as urethane isocyanate-derived materials, urea isocyanate-derived materials, urethane/urea isocyanate-derived materials, mixtures thereof, and the like. Further information on isocyanate-derived vehicle materials is disclosed in, for example, U.S. Pat. Nos. 5,750,604, 5,780,528, 5,782,966, 5,783,658, 5,827,918, 5,830,942, 5,919,839, 6,255,432, and 6,309,453, British Patents Nos. GB 2 294 939, GB 2 305 928, GB 2 305 670, and GB 2 290 793, and PCT Publications WO 94/14902, WO 97/12003, WO 97/13816, WO 96/14364, WO 97/33943, and WO 95/04760, the entire disclosures of each of which are incorporated herein by reference.

Examples of suitable ink vehicles include, for example, ethylene/propylene copolymers, such as those available from Baker Petrolite. Commercial examples of such copolymers include, for example, PETROLITE™ CP-7 (Mn=650), PETROLITE™ CP-11 (Mn=1,100, PETROLITE™ CP-12 (Mn=1,200) and the like. The copolymers may have, for example, a melting point of from about 70° C. to about 150° C., such as from about 80° C. to about 130° C. or from about 90° C. to about 120° C. and a molecular weight range (Mn) of from about 500 to about 4,000.

Urethane derivatives of oxidized synthetic or petroleum waxes, such as those available from Baker Petrolite and of the general formulas

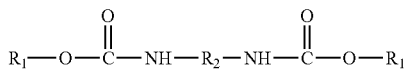

wherein $R_1$ is an alkyl group of the formula $CH_3(CH_2)_n$, n is an integer of from about 5 to about 200, for example from about 10 to about 150 or from about 10 to about 100 and $R_2$ is an arylene group, may also be used as the ink vehicle. These materials may have a melting point of from about 60° C. to about 120° C., such as from about 70° C. to about 100° C. or from about 70° C. to about 90° C. Commercial examples of such materials include, for example, BAKER PETROLITE™ CA-11 (Mn=790, Mw/Mn=2.2), PETROLITE™ WB-5 (Mn=650, Mw/Mn=1.7), PETROLITE™ WB-17 (Mn=730, Mw/Mn=1.8), and the like.

Another type of ink vehicle may be n-paraffinic, branched paraffinic, and/or naphthenic hydrocarbons, typically with from about 5 to about 100, such as from about 20 to about 80 or from about 30 to about 60 carbon atoms, generally prepared by the refinement of naturally occurring hydrocarbons, such as BE SQUARE 185 and BE SQUARE 195, with number average molecular weights (Mn) of from about 100 to about 5,000, such as from about 250 to about 1,000 or from about 500 to about 800, for example such as available from Baker Petrolite.

Highly branched hydrocarbons, typically prepared by olefin polymerization, such as the VYBAR materials available from Baker Petrolite, including VYBAR 253 (Mn=520), VYBAR 5013 (Mn=420), and the like, may also be used. In addition, the ink vehicle may be an ethoxylated alcohol, such as available from Baker Petrolite and of the general formula

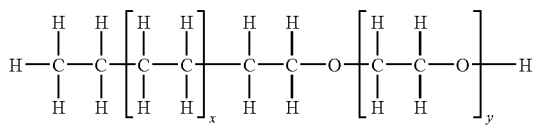

wherein x is an integer of from about 1 to about 50, such as from about 5 to about 40 or from about 11 to about 24 and y is an integer of from about 1 to about 70, such as from about 1 to about 50 or from about 1 to about 40. The materials may have a melting point of from about 60 to about 150° C., such as from about 70 to about 120° C. or from about 80 to about 110° C. and a number-average molecular weight (Mn) range of from about 100 to about 5,000, such as from about 500 to about 3,000 or from about 500 to about 2,500. Commercial examples include UNITHOX® 420 (Mn=560), UNITHOX® 450 (Mn=900), UNITHOX® 480 (Mn=2,250), UNITHOX® 520 (Mn=700), UNITHOX® 550 (Mn=1,100), UNITHOX® 720 (Mn=875), UNITHOX® 750 (Mn=1,400), and the like.

As an additional example, the ink vehicle may be made of fatty amides, such as monoamides, tetra-amides, mixtures thereof, and the like, for example such as described in U.S. Pat. No. 6,858,070, incorporated herein by reference. Suitable monoamides may have a melting point of at least about 50° C., for example from about 50° C. to about 150° C., although the melting point can be outside these ranges. Specific examples of suitable monoamides include, for example, primary monoamides and secondary monoamides. Stearamide, such as KEMAMIDE™ S available from Witco Chemical Company and CRODAMIDE™ S available from Croda, behenamide/arachidamide, such as KEMAMIDE™ B available from Witco and CRODAMIDE™ BR available from Croda, oleamide, such as KEMAMIDE™ U available from Witco and CRODAMIDE™ OR available from Croda, technical grade oleamide, such as KEMAMIDE™ O available from Witco, CRODAMIDE™ O available from Croda, and UNISLIP™ 1753 available from Uniqema, and erucamide such as KEMAMIDE™ E available from Witco and CRODAMIDE™ ER available from Croda, are some examples of suitable primary amides. Behenyl behenamide, such as KEMAMIDE EX666 available from Witco, stearyl stearamide, such as KEMAMIDE™ S-180 and KEMAMIDE™ EX-672 available from Witco, stearyl erucamide, such as KEMAMIDE™ E-180 available from Witco and CRODAMIDE™ 212 available from Croda, erucyl erucamide, such as KEMAMIDE™ E-221 available from Witco, oleyl palmitamide, such as KEMAMIDE™ P-181 available from Witco and CRODAMIDE™ 203 available from Croda, and erucyl stearamide, such as KEMAMIDE™ S-221 available from Witco, are some examples of suitable secondary amides. Additional suitable amide materials include KEMAMIDE™ W40 (N,N'-ethylenebisstearamide), KEMAMIDE™ P181 (oleyl palmitamide), KEMAMIDE™ W45 (N,N'-thylenebisstearamide), and KEMAMIDE™ W20 (N,N-ethylenebisoleamide).

High molecular weight linear alcohols, such as those available from Baker Petrolite and of the general formula

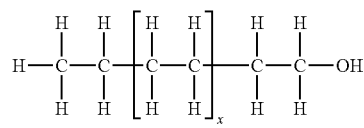

wherein x is an integer of from about 1 to about 50, such as from about 5 to about 35 or from about 11 to about 23, may also be used as the ink vehicle. These materials may have a melting point of from about 50 to about 150° C., such as from about 70 to about 120° C. or from about 75 to about 110° C., and a number-average molecular weight (Mn) range of from about 100 to about 5,000, such as from about 200 to about 2,500 or from about 300 to about 1,500. Commercial examples include the UNILIN® materials such as UNILIN® 425 (Mn=460), UNILIN® 550 (Mn=550), UNILIN® 700 (Mn=700), and distilled alcohols, the viscosity of which at the jetting temperature in one embodiment can be from about 5 to about 50% higher than the non-distilled alcohol.

A still further example includes hydrocarbon-based waxes, such as the homopolymers of polyethylene available from Baker Petrolite and of the general formula

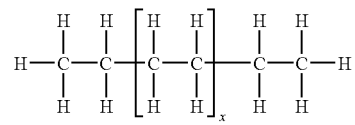

wherein x is an integer of from about 1 to about 200, such as from about 5 to about 150 or from about 12 to about 105. These materials may have a melting point of from about 60° C. to about 150° C., such as from about 70° C. to about 140° C. or from about 80° C. to about 130° and a molecular weight (Mn) of from about 100 to about 5,000, such as from about 200 to about 4,000 or from about 400 to about 3,000. Example waxes include PW400 (Mn about 400), distilled PW400, in one embodiment having a viscosity of about 10% to about 100% higher than the viscosity of the undistilled POLYWAX® 400 at about 110° C., POLYWAX 500 (Mn about 500), distilled POLYWAX® 500, in one embodiment having a viscosity of about 10% to about 100% higher than the viscosity of the undistilled POLYWAX® 500 at about 110° C., POLYWAX 655 (Mn about 655), distilled POLYWAX® 655, in one embodiment having a viscosity of about 10% to about 50% lower than the viscosity of the undistilled POLYWAX® 655 at about 110° C., and in yet another embodiment having a viscosity of about 10% to about 50% higher than the viscosity of the undistilled POLYWAX® 655 at about 110° C. POLYWAX® 850 (Mn about 850), POLYWAX® 1000 (Mn about 1,000), and the like.

Another example includes modified maleic anhydride hydrocarbon adducts of polyolefins prepared by graft copolymerization, such as those available from Baker Petrolite and of the general formulas

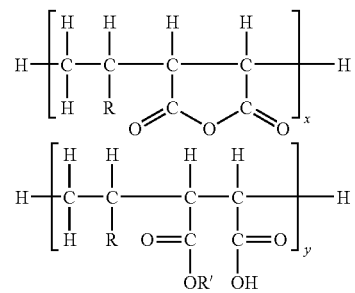

wherein R is an alkyl group with from about 1 to about 50, such as from about 5 to about 35 or from about 6 to about 28 carbon atoms, R' is an ethyl group, a propyl group, an isopropyl group, a butyl group, an isobutyl group, or an alkyl group with from about 5 to about 500, such as from about 10 to about 300 or from about 20 to about 200 carbon atoms, x is an integer of from about 9 to about 13, and y is an integer of from about 1 to about 50, such as from about 5 to about 25 or from about 9 to about 13, and having melting points of from about 50 to about 150° C., such as from about 60 to about 120° C. or from about 70 to about 100° C.; and those available from Baker Petrolite and of the general formula

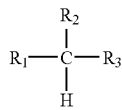

wherein $R_1$ and $R_3$ are hydrocarbon groups and $R_2$ is either of one of the general formulas

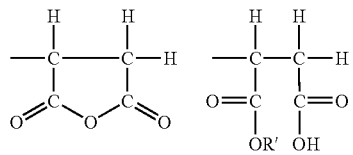

or a mixture thereof, wherein R' is an isopropyl group, which materials may have melting points of from about 70° C. to about 150° C., such as from about 80° C. to about 130° C. or from about 90° C. to about 125° C., with examples of modified maleic anhydride copolymers including CERAMER™ 67 (Mn=655, Mw/Mn=1.1), CERAMER™ 1608 (Mn=700, Mw/Mn=1.7), and the like.

Additional examples of suitable ink vehicles for the phase change inks include rosin esters; polyamides; dimer acid amides; fatty acid amides, including ARAMID™ C; epoxy resins, such as EPOTUF™ 37001, available from Riechold Chemical Company; fluid paraffin waxes; fluid microcrystalline waxes; Fischer-Tropsch waxes; polyvinyl alcohol resins; polyols; cellulose esters; cellulose ethers; polyvinyl pyridine resins; fatty acids; fatty acid esters; poly sulfonamides, including KETJENFLEX™ MH and KETJENFLEX™ MS80; benzoate esters, such as BENZOFLEX™ 5552, available from Velsicol Chemical Company; phthalate plasticizers; citrate plasticizers; maleate plasticizers; sulfones, such as diphenyl sulfone, n-decyl sulfone, n-amyl sulfone, chlorophenyl methyl sulfone; polyvinyl pyrrolidinone copolymers; polyvinyl pyrrolidone/polyvinyl acetate copolymers; novolac resins, such as DUREZ™ 12 686, available from Occidental Chemical Company; and natural product waxes, such as beeswax, monton wax, candelilla wax, GILSONITE™ (American Gilsonite Company), and the like; mixtures of linear primary alcohols with linear long chain amides or fatty acid amides, such as those with from about 6 to about 24 carbon atoms, including PARICIN™ 9 (propylene glycol monohydroxystearate), PARICIN™ 13 (glycerol monohydroxystearate), PARICIN™ 15 (ethylene glycol monohydroxystearate), PARICIN™ 220 (N(2-hydroxyethyl)-12-hydroxystearamide), PARICIN 285 (N,N'-ethylene-bis-12-hydroxystearamide), FLEXRICIN™ 185 (N,N'-ethylene-bis-ricinoleamide), and the like. Further, linear long chain sulfones with from about 4 to about 16 carbon atoms, such as n-propyl sulfone, n-pentyl sulfone, n-hexyl sulfone, n-heptyl sulfone, n-octyl sulfone, n-nonyl sulfone, n-decyl sulfone, n-undecyl sulfone, n-dodecyl sulfone, n-tridecyl sulfone, n-tetradecyl sulfone, n-pentadecyl sulfone, n-hexadecyl sulfone, and the like, are suitable ink vehicle materials.

In addition, the ink vehicles described in U.S. Pat. No. 6,906,118, incorporated herein by reference, may also be used. The ink vehicle may contain a branched triamide such as those described in U.S. Pat. No. 6,860,930, the disclosure of which is totally included here by reference.

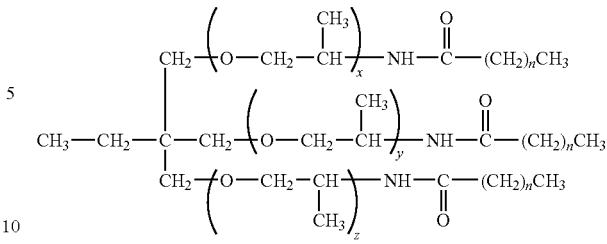

wherein n has an average value of from about 34 equal to or less than 40, where x, y and z can each be zero or an integer, and wherein the sum of x, y, and z is from about 5 and equal to or less than 6.

The ink vehicle may comprise one or more of the aforementioned suitable materials.

The ink vehicles for the phase change inks may have melting points of from about 60 to about 150° C., for example from about 80 to about 120° C. or from about 85 to about 110° C., as determined by, for example, observation and measurement on a microscope hot stage, wherein the binder material is heated on a glass slide and observed by microscope. Higher melting points are also acceptable, although printhead life may be reduced at temperatures higher than 150° C.

In addition, the surface tension of the ink at the operating (jetting) temperature of the ink should be from about 20 to about 40 dynes per centimeter, for example from about 40 to about 65 dynes per centimeter, to enhance refill rates and color mixing. The operating, or jetting, temperatures of the phase change inks generally are from about 60 to about 150° C. The viscosity of the ink at the operating temperature of the ink is generally from about 1 to about 20 cP, for example from about 1 to about 15 cP or from about 5 to about 15 cP.

The ink composition as a whole generally includes the ink vehicle (that is, exclusive of pigment particles, and the like) in an amount of from about 25% to about 99.5% by weight of the ink, for example from about 30% to about 90% or from about 50% to about 85% by weight of the ink.

Pigment

The phase change inks of the disclosure contain at least one pigment. The pigment is present in the ink in any desired amount, typically from about 0.5 to about 30 percent by weight of the ink vehicle or ink vehicle/propellant mixture, for example from about 1 to about 50 percent by weight of the ink vehicle or ink vehicle/propellant mixture. In one embodiment, the ink may contain a mixture of at least two different pigments.

Examples of suitable pigments include, but are not limited to, Violet PALIOGEN Violet 5100 (BASF); PALIOGEN Violet 5890 (BASF); HELIOGEN Green L8730 (BASF); LITHOL Scarlet D3700 (BASF); Sunfast® Blue 15:4 (Sun Chemical 249-0592); Hostaperm Blue B4-G (Clariant); Hostaperm Blue B2G-D (Clariant); Permanent Red P-F7RK; Hostaperm Violet BL (Clariant); LITHOL Scarlet 4440 (BASF); Bon Red C (Dominion Color Company); ORACET Pink RF (Ciba); PALIOGEN Red 3871 K (BASF); Sunfast® Blue 15:3 (Sun Chemical 249-1284); PALIOGEN Red 3340 (BASF); Sunfast® Carbazole Violet 23 (Sun Chemical 246-1670); LITHOL Fast Scarlet L4300 (BASF); Sunbrite Yellow 17 (Sun Chemical 275-0023); HELIOGEN Blue L6900, L7020 (BASF); Sunbrite Yellow 74 (Sun Chemical 272-0558); Spectra Pac® C Orange 16 (Sun Chemical 276-3016); HELIOGEN Blue K6902, K6910 (BASF); Sunfast® Magenta 122 (Sun Chemical 228-0013); HELIOGEN Blue D6840, D7080 (BASF); Sudan Blue OS (BASF); NEOPEN Blue FF4012 (BASF); PV Fast Blue B2GO1 (Clariant); IRGALITE Blue BCA (Ciba); PALIOGEN Blue 6470 (BASF); Sudan Orange G (Aldrich), Sudan Orange 220 (BASF); PALIOGEN Orange 3040 (BASF); PALIOGEN Yellow 152, 1560 (BASF); LITHOL Fast Yellow 0991 K (BASF); PALIOTOL Yellow 1840 (BASF); NOVOPERM Yellow FGL (Clariant); Lumogen Yellow D0790 (BASF); Suco-Yellow L1250 (BASF); Suco-Yellow D1355 (BASF); Suco Fast Yellow D1355, D1351 (BASF); HOSTAPERM Pink E 02 (Clariant); Hansa Brilliant Yellow 5GX03 (Clariant); Permanent Yellow GRL 02 (Clariant); Permanent Rubine L6B 05 (Clariant); FANAL Pink D4830 (BASF); CINQUASIA Magenta (DU PONT), PALIOGEN Black L0084 (BASF); Pigment Black K801 (BASF); and carbon blacks such as REGAL 330™ (Cabot), Carbon Black 5250, Carbon Black 5750 (Columbia Chemical), mixtures thereof and the like.

In some embodiments, the pigment is a magenta pigment such as pigment red 57.1 pigment. Suitable magenta pigments include those that have a primary average particle size range from about 50 to about 200 nm as determined by transmission electron microscopy according to ASTM 3849, more preferably a particle size range of 50 to 150 nm. The average primary particle size indicates the size of the primary particles of pigment present in the ink; these primary particles may form aggregates of two or more particles when present in the ink.

Other Components in the Ink

Optionally, a propellant may be contained in the phase change ink, although it is not required in many ink compositions. Suitable propellants for the phase change inks, present in any effective amount such as from about 10 to about 90 percent by weight, for example from about 20 to about 50 percent by weight, of the ink generally have melting points of from about 50 to about 150° C., for example from about 80 to about 120° C. In another embodiment, the propellants generally have a boiling point of from about 180 to about 250° C., for example from about 200 to about 230° C. Further, the surface tension of the propellant in its liquid state at the operating temperature of the ink may be from about 20 to about 65 dynes per centimeter, for example from about 40 to about 65 dynes per centimeter, to enhance refill rates, paper wetting, and color mixing. In addition, the propellants ideally have a viscosity at the operating temperature of the ink of from about 1 to about 20 centipoise, for example from about 1 to about 5 centipoise, to enhance refill and jettability. The propellant may also be thermally stable in its molten state so that it does not undergo decomposition to yield gaseous products or to form heater deposits.

The ink can also contain an antioxidant. The antioxidants of the ink compositions protect the ink components from oxidation during the heating portion of the ink preparation and jetting processes. Specific examples of suitable antioxidants are set forth in U.S. Pat. No. 6,858,070, the disclosure of which is totally incorporated herein by reference. When present, the optional antioxidant is present in the ink in any desired or effective amount, in one embodiment of at least about 0.01% by weight of the ink vehicle, in another embodiment of at least about 0.1% by weight of the ink vehicle, and in yet another embodiment of at least about 1% by weight of the ink vehicle, and in one embodiment of equal to or less than about 20% by weight of the ink vehicle, in another embodiment equal to or less than about 5% by weight of the ink vehicle, and in yet another embodiment equal to or less than about 3% by weight of the ink vehicle, although the amount can be outside of these ranges. When only one antioxidant is used, a hindered amine is preferred, e.g.: NAUGARD™ 445 antioxidant (obtained from Uniroyal Chemical Co., Middlebury, Conn. or Crompton Corporation) In other embodiments, mixtures of antioxidants used to improve melt processing stability and long-term thermal stability include, but are not limited to, hindered amines, phosphites, hindered phenols, hydroxylamines, lactones, tocopherols, thiosynergists, and the like.

The ink disclosed herein can also contain resins and waxes such as: CRODAMIDE™ 203 (commercially available from Croda), CRODAMIDE™ ORX (commercially available from Croda), KEMAMIDE™ S-180 and E-180 (commercially available from Witco), UNISLIP™ 1750 (commercially available from Uniqema), UNICLEAR™ 80 (commercially available from Arizona), a dicapryladipate compatibilizer such as ARIZONA™ SP-100, VYBAR™ 263 and 243 (commercially available from Baker Petrolite), 1-docosanol (commercially available from Aldrich), UNILIN™ 700 (commercially available from Baker Hughes), Beeswax Cerra Bellina (commercially available from Kester Keunen), branched BK-42 ester (commercially available from Kester Keunen), Kester Wax K-82-D, hydroxypolyester K-82-P, synthetic Karnauba K-82-H, Siliconyl Beeswax (commercially available from Kester Keunen), stearyl alcohol 98 NF (commercially available from Kester Keunen), KRATON™ D1101 (commercially available from Kraton Polymers), Behenyl Behenate, straight chain even numbered mono esters having a carbon chain from C-40 to C44 (commercially available from Kester Keunen as KESTER™ WAX 72), synthetic paraffin wax of a sharp melting point such as CALLISTA 158 (commercially available from Shell), microcrystalline branched hydrocarbon waxes such as MICROWAX™ HG (commercially available from Paramelt), Mp=80-86, and MICROWAX™ P827, KEMAMIDE™ 5-221, polyethyleneglycol 400 distearate (commercially available from Mosselman); paraffin waxes such as HINP-9 and HNP-12 (commercially available from Nippon Seiro Co.); semi-crystalline wax such as HIMIC-2065 (commercially available from Nippon Seiro Co.); hydrogenated styrene-butadiene copolymers of low molecular weight such as TUFTEC™ H114.11102 (commercially available from Asahi Kasei Corp); ethylene-propylene copolymers such as EP-700 and EP-602 (commercially available from Baker Hughes); UNITHOX™ 420 ethoxylate (commercially available from Baker Hughes); propylene-ethylene copolymer alcohols of melting point in the range of 65 to 100° C. (commercially available from Baker Hughes); maleic anhydride mono-isopropyl maleate such as CERAMER™ 1251 (commercially available from Baker Hughes); alpha olefin-maleic anhydride polymer of melting point of about 80 degree C. (commercially available from Baker Petrolite) (X-5399); oxidized ethene homopolymer, PETROLITE™ C-9500 (commercially available from Baker Hughes); oxidized 1-propene with ethane, CARDIS™ 314 (commercially available from Baker Hughes), Victory Amber wax (commercially available from Bareco), oxidized PE such as OX-020T (commercially available from Nippon Seiro Co.). The ink can also contain paraffin waxes and microcrystalline waxes. Paraffin wax is a straight chain hydrocarbon having a melting point of about 49 to 71 degree C.; microcrystalline wax is separated from asphalts and is higher in MW and more branched than the paraffin wax. The melting point of microcrystalline waxes is between 60 and 89° C. Examples of suitable paraffin waxes are HNP-3, 5, 9, 10, 11 and HNP-12 (commercially available from Nippon Seiro Co.).

The inks of embodiments may further include conventional additives to take advantage of the known functionality associated with such conventional additives. Such additives may include, for example, defoamers, slip and leveling agents, plasticizers, pigment dispersants, etc.

Other optional additives such as plasticizers may be present in the inks. Plasticizers that may be used include pentaerythritol tetrabenzoate, commercially available as BENZOFLEX S552 (Velsicol Chemical Corporation), trimethyl titrate, commercially available as CITROFLEX 1 (Monflex Chemical Company), N,N-dimethyl oleamide, commercially available as HALCOMID M-18-OL (C. P. Hall Company), and the like, may be added to the ink vehicle, and may constitute from about 0.5 to 20 percent of the ink vehicle component of the ink. Plasticizers can either function as the ink vehicle or can act as an agent to provide compatibility between the ink propellant, which generally is polar, and the ink vehicle, which generally is non-polar.

Preparation of the Ink

Preparation of pigmented phase change ink compositions can include the partial or total inclusion of ink components therein during the act of pigment dispersion making. This can also include the dispersing of pigment at various pigment concentrations at various temperatures with various inputted energies. The pigment can be processed, with or without at least one dispersant, such that it is dispersed by various means including ball mills, attritors, Cobol mills, Dyno mills, paint shakers, pearl mills, agitator mills, two-roll mills, high speed stirring, three-roll mills, flow jet mills, extruders, homogenizers, kneaders and the like.

The pigment can be optionally processed with suitable grinding media in any of the aforementioned dispersing equipment, where it is applicable, such as steel balls, glass balls, glass beads, polyethylene beads, Nylon beads, ceramic beads and the like. The phase change ink compositions may be prepared by combining some or all of the components, heating the mixture to at least its melting point, for example from about 70 to about 120° C., and stirring the mixture, until a substantially homogeneous and uniform melt is obtained. For example, the molten mixture may be subjected to grinding in an attritor or ball mill apparatus to effect dispersion of the pigment in the ink vehicle.

The phase change ink can also be prepared by first admixing in an extruder the pigment together with the dispersant, or part of the ink ingredients in an extruder, at the optimum process conditions to shear and wet the pigment. The resulting pigment dispersion should have a viscosity sufficiently low to enable mixing in the extruder, and also sufficiently high to enable a desirable degree of shear to be generated within the extruder. Any desired or effective extruder can be employed, including single screw extruders, twin screw extruders, including co-rotating twin screw extruders (wherein both screws rotate in the same direction), counter-rotating twin screw extruders (wherein the screws rotate in opposite directions), and the like. Admixing the resulting pigment dispersion with the additional ink carrier ingredients and any desired additional optional ingredients and subjecting the resulting mixture to high shear agitation using the equipments as mentioned above to prepare the ink.

Use of the Ink

Printed images may be generated with the inks described herein by incorporating one or more inks into a printer cartridge that is used in an ink jet device, for example a thermal ink jet device, an acoustic ink jet device or a piezoelectric ink jet device, and concurrently causing droplets of the inks to be ejected in an imagewise pattern onto an image receiving substrate such as paper or transparency material. Each ink of the ink sets is typically included in a reservoir connected by any suitable feeding device to the corresponding ejecting channels of the ink jet head. In the jetting procedure, the ink jet head may be heated, by any suitable method, to the jetting temperature of the inks.

The inks can also be employed in indirect printing ink jet applications, wherein when droplets of the melted ink are ejected in an imagewise pattern onto an image receiving substrate, the substrate is an intermediate transfer member and the ink in the imagewise pattern is subsequently transferred from the intermediate transfer member to a final recording substrate. The intermediate transfer member may be, for example, a drum.

In embodiments using an intermediate transfer member, the member may be heated to have a temperature on a surface thereof of from about 45 to about 80° C. The elevated surface temperature permits the ink to remain in a molten state while avoiding offset or ink splitting on the surface of the transfer member, thereby enabling good transfer of the image to the end image receiving substrate such as paper or transparency.

In embodiments, the ink jet system thus includes the aforementioned inks in an ink set comprised of at least three differently colored phase change inks, such as cyan, magenta, yellow and black inks. The system also includes an ink jet device including an ink jet head consisting of one channel for each one of the differently colored phase change inks in the ink set, and a supply path that supplies each of the differently colored phase change inks to the respective channels of the ink jet head, for example from reservoirs containing each of the differently colored phase change inks.

Any suitable substrate or recording sheet can be employed, including plain papers such as XEROX® 4200 papers XEROX® 4024 papers, XEROX® Image Series papers, Courtland 4024 DP paper, ruled notebook paper, bond paper, silica coated papers such as Sharp Company silica coated paper, JuJo paper, Hammermill Laserprint Paper, and the like, transparency materials, fabrics, textile products, plastics, polymeric films, inorganic substrates such as metals and wood, and the like.

It is desirable that the pigmented ink have certain attributes that include having good filterability, remain stable over several successive freeze thaw cycles, and have good rheological stability for at least 10 days at 120° C. Furthermore, the inks do not show any significant settling after 7 days at 120° C., or after 14 days at 120° C. The disclosed inks, in embodiments, exhibit Newtonian rheology properties, in addition to improved stability. The disclosed pigmented inks can be printed over a temperature range of about 100° C. to about 150° C., however, it is advantageous to print at relatively lower temperatures to further reduce printing costs by reducing energy consumption. These properties indicate that the inks include well-dispersed pigment particles with no evidence of pigment particle flocculation and settling. The pigmented ink stability is monitored using any number of suitable Dynamic Light Scattering apparatuses, such as a Malvern Zetasizer. For instance, the Z-average particle size over time can be monitored to gauge the stability of the pigment particles in the ink while it is held at elevated temperatures, such as about 120° C.

Embodiments described above will now be further illustrated by way of the following examples. These examples are intended to be illustrative, and the claims are not limited to the materials, conditions, or process parameters set forth in these embodiments.

EXAMPLES

Synthesis of Dispersants
The following dispersant compounds were synthesized as follows.

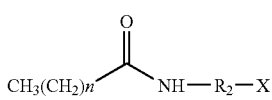

TABLE 1

| Example # | n average | Diamine | Salt Source | Synthesis Process |
|---|---|---|---|---|
| 1 | 28 | N,N-dimethyl-1-propyl amine | Dimethyl sulfate | Two pot process |
| 2 | 36 | N,N-dimethyl-1-propyl amine | Dimethyl sulfate | Two pot process |
| 3 | 46 | N,N-dimethyl-1-propyl amine | Dimethyl sulfate | Two pot process |
| 4 | 46 | N,N-dimethyl-1-propyl amine | Dimethyl sulfate | One pot process |
| 5 | 46 | N,N-dimethyl-1-propyl amine | Methyl p-toluene sulfonate | Two pot process |
| 6 | 46 | aminopropylmorpholine | Dimethyl sulfate | Two pot process |

Dispersant Example 1

In a 2 liter resin kettle fitted with heating mantle, mechanical stirring, Dean-Stark trap, reflux condenser and temperature sensor were introduced 246.05 g Unicid 425™ (a monoacid from Baker Petrolite of formula $CH_3(CH_2)_nCOOH$ wherein n has an average value of 28 carbons and is believed to have a range from about 20 to about 40) and N,N-dimethyl-1-propyl amine (35.76 g) from Aldrich. Under a stream of Argon, the temperature in the kettle was raised to 90° C. and the resin was allowed to melt. When the resin was completely melted, the temperature was gradually raised to 180° C. with stirring, and the reaction was allowed to proceed for 5 hours. Water (4 ml) was collected into the Dean-Stark trap. The reaction was stopped, cooled down to 120° C. and discharged in aluminum tray to give 243 g of the precursor amide. The amide precursor (150 g) was added to a 2 L resin kettle fitted with heating mantle, mechanical stirring, Dean-Stark trap, reflux condenser and temperature sensor. Toluene (300 ml) was added to the reaction flask. Under a stream of argon, the temperature was gradually raised to 100° C. during which the precursor amide dissolved. Dimethyl Sulfate 16.8 g) was slowly added through a syringe. The reaction was kept at 100° C. for 3 hours. The temperature was raised to 130° C. and Toluene started to distill off. The temperature was slowly raised until it reached 180° C. A vacuum was applied to remove excess toluene and dimethyl sulfate for 30 minutes. Vacuum was replaced with Argon and the reaction was stopped and discharged in Al trays to give the salt as a light brown solid (146 g; acid number, 14.86, amine number 4.10).

Dispersant Example 2

Dispersant Example 2 was prepared using the same procedure outlined for Dispersant Example 1 above, except Unicid 550™ (a monoacid from Baker Petrolite of formula $CH_3(CH_2)_nCOOH$ wherein n has an average value of 36 carbons and is believed to have a range from about 34 to about 40) was used in place of Unicid 425™ at the following scale: Unicid 550 (250 g), N,N-dimethyl-1-propyl amine (32.83 g), amide precursor (200 g), dimethyl sulfate (23.4 g), Toluene (240 ml). The product was obtained as a light brown solid (208 g; acid number 8.49, amine number 1.14).

Dispersant Example 3

Dispersant Example 3 was prepared using the same procedure outlined for Dispersant Example 1 above, except Unicid 700™ (a monoacid from Baker Petrolite of formula $CH_3(CH_2)_nCOOH$ wherein n has an average value of 46 carbons and is believed to have a range from about 40 to about 52) was used in place of Unicid 425™ at the following scale: Unicid 700 (481.15 g), N,N-dimethyl-1-propyl amine (48.02 g), amide precursor (452 g), dimethyl sulfate (34.2 g), Toluene (500 ml). The product was obtained as a light brown solid (486 g; acid number 9.96, amine number 6.54). $^1$H NMR analysis ($C_6D_6$, 500 MHz, at 70° C.) showed the amide precursor to be present at 11 mol %.

Dispersant Example 4

Dispersant Example 4 was made using a one pot process. In a 1 L resin kettle fitted with heating mantle, mechanical stirring, Dean-Stark trap, reflux condenser and temperature sensor were introduced 259 g Unicid 700™ resin and 26.5 g N,N-dimethyl-1-propyl amine (Huntsman). Under a stream of Argon, the temperature in the kettle was raised to 90° C. and the resin was allowed to melt. When the resin was completely melted, the temperature was gradually raised to 180° C. with stirring, and the reaction was allowed to proceed for 3 hours. Water (7.8 ml) was collected into the Dean-Stark trap. After 3 hours of reaction at 180° C., the temperature in the kettle was lowered to 150° C. When the temperature reached 150° C., 21.2 g dimethyl sulfate were added drop wise to the mixture over a period of 15 minutes, at a rate of about 1 ml/minute. At the end of the addition the reaction was allowed to stir for 1 hour at 150° C. The temperature was raised to 180° C., and the kettle was emptied warm. The salt was obtained as a light brown solid (275 g product, acid number 9.39, amine number 8.59).

Dispersant Example 5

Dispersant Example 5 was prepared using the same procedure outlined for Dispersant Example 3 above, except methyl p-toluene sulfonate was used in place of dimethyl sulfate at the following scale: amide precursor (200 g), methyl p-toluene sulfonate (29.0 g), Toluene (240 ml). The product was obtained as a light brown solid (231 g; acid number, 5.87, amine number 4.24).

Dispersant Example 6

Dispersant Example 6 was prepared using the same procedure outlined for Dispersant Example 3 above, except aminopropylmorpholine was used in place of N,N-dimethyl-1-propyl amine at the following scale: Unicid 700™ (200 g), aminopropylmorpholine (28.17 g), Amide precursor (150 g), dimethyl sulfate (12.53 g), Toluene (180 ml). The product was obtained as a light brown solid (157 g; acid number 13.9, amine number<1).

The Dispersant Examples 1-6 were found to have the following properties:

TABLE 2

| Example | IR (ammonium salt peak) (cm$^{-1}$) | Onset of Crystallization (° C.) | Peak of Crystallization (° C.) | Peak of Melting (° C.) | End of Melting (° C.) |
|---|---|---|---|---|---|
| 1 | 1223 | 92.4 | 89.7 | 87.7 | 107.6 |
| 2 | 1229 | 99.8 | 96.4 | 102.4 | 109.9 |
| 3 | 1224 | 100 | 95.6 | 104.6 | 117.8 |
| 4 | 1125 | 97.6 | 94.8 | 100.5 | 112.1 |
| 5 | 1190 | 98.3 | 96.2 | 103.5 | 108.5 |
| 6 | 1221 | 100.2 | 94 | 105.6 | 114 |

Preparation of Inks

Comparative Example 1

The following components were used to make a jettable solid ink, the amounts of which are given as parts by weight unless otherwise stated. An ink concentrate base was prepared by mixing the following components by melting and homogeneously blended them together at 120° C. using an overhead stirrer: 37.53 parts of a distilled Polyethylene Wax from Baker Petrolite, 20.00 parts triamide wax (triamide described in U.S. Pat. No. 6,860,930), 20.00 parts S-180 (a stearyl stearamide) commercially available from Crompton Corporation, 20.00 parts KE-100 resin commercially available from Arakawa Corporation, triglycerides of hydrogenated abietic (rosin) acid, from Arakawa Chemical Industries, Ltd., 2.26 parts of FORAL®. 85, an ester of a hydrogenated resin, available from Hercules Incorporated, 0.21 parts NAUGARD™ 445 available from Crompton Corporation, and 3.23 parts SOLSPERSE™ 17000, available from Lubrizol Corporation. A SZEGVARI™ 01 attritor pre-heated to 110° C. was charged with 1800 g ⅛" 440 C Grade 25 stainless steel balls, available from Hoover Precision Products, Incorporated, that were preheated to 120° C. The attritor was allowed to equilibrate for 30 minutes upon which 4.84 parts of Permanent Rubine L5B 01 pigment available from Clariant GmbH were added slowly to the ink base. A multi-staged impeller was then attached to the attritor and the speed adjusted to give an impeller tip velocity of about 7 cm/s. The pigmented mixture was allowed to attrite overnight for 19 hours upon which the resultant ink pigment concentrate showed excellent free-flowing behavior when it was discharged and separated from the steel balls in its molten state.

The ink of Comparative Example 1 was then made from the ink pigment concentrate discussed above. Specifically, 70.1 g of a molten homogeneous solution of the following components mixture was prepared: 72.98 parts of a distilled Polyethylene Wax from Baker Petrolite, 3.70 parts triamide wax (triamide described in U.S. Pat. No. 6,860,930), 17.11 parts S-180 (a stearyl stearamide) commercially available from Crompton Corporation, 5.20 parts KE-100 resin commercially available from Arakawa Corporation, triglycerides of hydrogenated abietic (rosin) acid, from Arakawa Chemical Industries, Ltd., 0.23 parts Naugard 445 available from Crompton Corporation, and 0.78 parts Solsperse 17000, available from Lubrizol Corporation. This solution was added slowly to 74.9 g of the ink pigment concentrate from Comparative Example 1 in an oven at 120° C. while stirring at 400 RPM. The resulting pigmented ink was coarsely filtered at 120° C. past a 6 micron glass fiber filter available commercially from Pall Corporation. Thereupon the ink was filtered through a 1 micron glass fiber filter available commercially from Pall Corporation. The shear rate viscosity at 115° C. was measured on the 1 micron permeate of the ink using cone and plate method on an RFS3 rheometer available from Rheometrics Scientific. The ink was found to be Newtonian and had shear rate viscosities of 10.0 and 9.9 cP at 1 and 100 s$^{-1}$, respectively.

Comparative Example 2

An ink pigment concentrate was made in the same manner as in Comparative Example 1, except that in place of Solsperse 17000, 3.23 parts of the amide precursor from dispersant Example 3 were used.

From this ink pigment concentrate an ink was prepared. The making of this ink concentrate proceeded in the same manner as in Comparative Example 1, except that in place of Solsperse 17000, 0.78 parts of the amide precursor of dispersant Example 3 were used. The resulting pigmented ink was coarsely filtered at 120° C. past a 6 μm glass fiber filter, available commercially from Pall Corporation. Thereupon the ink was filtered through a 1 micron glass fiber filter, available commercially from Pall Corporation. The shear rate viscosity at 115° C. was measured on the 1 micron permeate of the ink using cone and plate method on an RFS3 rheometer available from Rheometrics Scientific. The ink was found to be Newtonian and had shear rate viscosities of 14.7 and 11.2 cP at 1 and 100 s$^{-1}$, respectively.

Example 1

An ink pigment concentrate was made in the same manner as in Comparative Example 1, except that in place of Solsperse 17000, 3.23 parts of the dispersant Example 3 were used.

From this ink pigment concentrate an ink was prepared. The making of this ink concentrate proceeded in the same manner as in Comparative Example 1, except that in place of Solsperse 17000, 0.78 parts of the dispersant Example 3 were used. The resulting pigmented ink was coarsely filtered at 120° C. past a 6 μm glass fiber filter available commercially from Pall Corporation. Thereupon the ink was filtered through a 1 micron glass fiber filter available commercially from Pall Corporation. The shear rate viscosity at 115° C. was measured on the 1 micron permeate of the ink using cone and plate method on an RFS3 rheometer available from Rheometrics Scientific. The ink was found to be Newtonian and had shear rate viscosities of 10.3 and 10.5 cP at 1 and 100 s$^{-1}$, respectively.

Example 2

Example 2 proceeded as a different process for the making of the ink as described in Example 1. First, a pigment extrudate was prepared according to the following procedure.

Tri-amide resin, Tri-A-37 was prepared as described in U.S. Pat. No. 6,860,930. Originally in the form of chips or chunks it was processed through a grinder to powder form. Thereafter, 700.55 parts of the pulverized tri-amide resin and 155.13 parts of Permanent Rubine L5B 01 pigment available from Clariant GmbH and 126.95 parts of dispersant Example 3 (processed through a grinder in powdered form) were admixed in a LITTLEFORD M5 blender for 30 minutes at 0.8 A. Subsequently, the powder mixture was added at a rate of 0.8 lbs/hr to a DAVO counter-rotating twin screw extruder (Model VS 104, from Deutsche Apparate-Vertrieborganisation GmbH & Co, Troisdorf, Germany) heated at 70° C. The molten contents in the extruder were then mixed at 50 RPM and discharged through a strand die at 75° C. Finally, the extruded dispersion, Extrudate X, was melt-mixed with other ink ingredients to form an ink.

Next, an ink was prepared from the pigment extrude, as follows. The following components were melted and stir-mixed in a 2 L beaker (A) at 125° C.: Extrudate X as discussed above (158.4 parts), FORAL®. 85, an ester of a hydrogenated resin, available from Hercules Incorporated (2.8 parts), KEMAMIDE™ S180 from Crompton Corp. (186.89 parts), KE100 resin from Arakawa Chemical Industries Ltd (120.10 parts), and NAUGARD™ N445 from Crompton Corp. (2.10 parts g). Beaker (A) was equipped with a heating mantel and a mechanical stirrer. The pigment dispersion was heated and stirred for 90 min. at 120° C. While the pigment dispersion was being prepared in beaker (A), a polyethylene wax X1197 from Baker Petrolite (529.75 parts) was melted inside a Beaker (B) equipped with a heating mantel and a mechanical stirrer. The resin dispersion in beaker (B) was heated and stirred at 12° C. for an hour to ensure that the resin was fully melt-mixed.

An IKA Ultra Turrax T50 Homogenizer was then used to homogenize the ingredients in beaker (A) for 18 minutes with the temperature maintained at 120° C. during homogenization. The molten resin in beaker (B), which was kept at 120° C. was then added into the homogenized pigment dispersion in beaker (A). The resulting mixed ink dispersion in beaker (A) was further homogenized for an additional 36 minutes. After filtering the resulting ink through a 1 micron Parker filter the ink was cooled to room temperature and thereafter its rheology was measured using the AR2000 rheometer. The shear rate viscosity at 115° C. was measured on the 1 micron permeate of the ink using cone and plate method on an RFS3 rheometer available from Rheometrics Scientific. The ink was found to be Newtonian and had shear rate viscosities of 9.05 and 9.22 cP at 1 and 100 $s^{-1}$, respectively.

Example 3

Example 3 proceeded according to the process described in Example 1, except that 3.23 grams of dispersant Example 1 were used in place of dispersant Example 3 during the making of the ink pigment concentrate, and 0.78 grams of dispersant Example 1 were used in place of dispersant Example 3 during the making of the ink from the concentrate. The resulting pigmented ink was coarsely filtered at 120° C. past a 6 µm glass fiber filter, available commercially from Pall Corporation. Thereupon the ink was filtered through a 1 micron glass fiber filter, available commercially from Pall Corporation. The shear rate viscosity at 115° C. was measured on the 1 micron permeate of the ink using cone and plate method on an RFS3 rheometer available from Rheometrics Scientific. The ink was found to be Newtonian and had shear rate viscosities of 10.3 and 10.5 cP at 1 and 100 $s^{-1}$, respectively.

Example 4

Example 4 proceeded according to the process described in Example 1, except that 3.23 grams of dispersant Example 2 were used in place of dispersant Example 3 during the making of the ink pigment concentrate, and 0.78 grams of dispersant Example 2 were used in place of dispersant Example 3 during the making of the ink from the concentrate. The resulting pigmented ink was filtered at 120° C. past through a 1 micron glass fiber filter, available commercially from Pall Corporation. The shear rate viscosity at 115° C. was measured on the 1 micron permeate of the ink using cone and plate method on an RFS3 rheometer available from Rheometrics Scientific. The ink was found to be Newtonian and had shear rate viscosities of 9.7 and 10.0 cP at 1 and 100 $s^{-1}$, respectively.

Example 5

Example 5 proceeded according to the process described in Example 1, except that dispersant Example 5 were used in place of dispersant Example 3. After filtering the resulting ink through a 1 micron Parker filter the ink was cooled to room temperature. The shear rate viscosity at 115° C. was measured on the 1 micron permeate of the ink using cone and plate method on an RFS3 rheometer available from Rheometrics Scientific. The ink was found to be Newtonian and had shear rate viscosities of 8.1 and 9.6 cP at 1 and 100 $s^{-1}$, respectively.

Example 6

Example 6 proceeded according to the process described in Example 2, except that 3.23 grams of dispersant Example 6 were used in place of dispersant Example 3 during the making of the ink pigment concentrate, and 0.78 grams of dispersant Example 6 were used in place of dispersant Example 3 during the making of the ink from the concentrate. The resulting pigmented ink was coarsely filtered at 120° C. past a 6 µm glass fiber filter, available commercially from Pall Corporation. Thereupon the ink was filtered through a 1 micron glass fiber filter, available commercially from Pall Corporation. The shear rate viscosity at 115° C. was measured on the 1 micron permeate of the ink using cone and plate method on an RFS3 rheometer available from Rheometrics Scientific. The ink was found to be Newtonian and had shear rate viscosities of 11.4 and 9.9 cP at 1 and 100 $s^{-1}$, respectively.

Some of the above discussed inks were next tested to determine the degree of pigment agglomeration over time. Four inks (comparative examples 1 and 2, example 1 and example 2) were aged in an oven at 120° C. and the Z-average particle size, herein referred to as particle size, was measured at 112° C. using a Malvern Zetasizer particle size analyzer. As shown in FIG. 1, the two inks made according to this disclosure (Example 1 and Example 2) had stable particle size over 14 days. Furthermore, the ink of Example 2 was additionally aged for over 3 months at 120° C. and still showed very little or no particle size growth. In contrast, Comparative Example 1 made with the commercial dispersant showed extensive particle size growth while being aged after only 2 days at 120° C.

Figure 2:
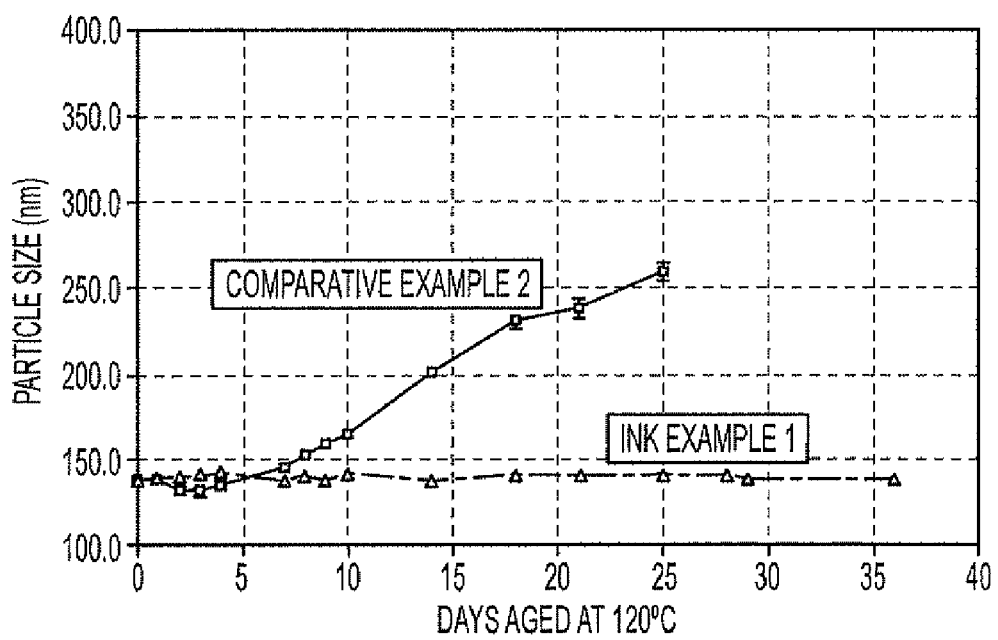
FIG. 2 shows pigment Z-average particle sizes over time of phase change ink example 1 comprising dispersant example 3 compared to comparative ink example 2.

In a manner similar to the testing described directly above, Example 1 was compared to Comparative Example 2. The results are shown in FIG. 2. As can be seen in the figure, the ink of Comparative Example 2 made from the amide precursor from example 3 experienced pigment particle growth (i.e. agglomeration) after about 8 days. This indicates that the anchor group is essential to preventing agglomeration. Nonetheless, Comparative Example 2 still performed better than Comparative Example 1 (particle size below 200 nm after 10 days compared to 1000 nm for the commercial dispersant after 6 days), highlighting the importance the dispersant's chain length has on particle size stability, as well.

Figure 3:
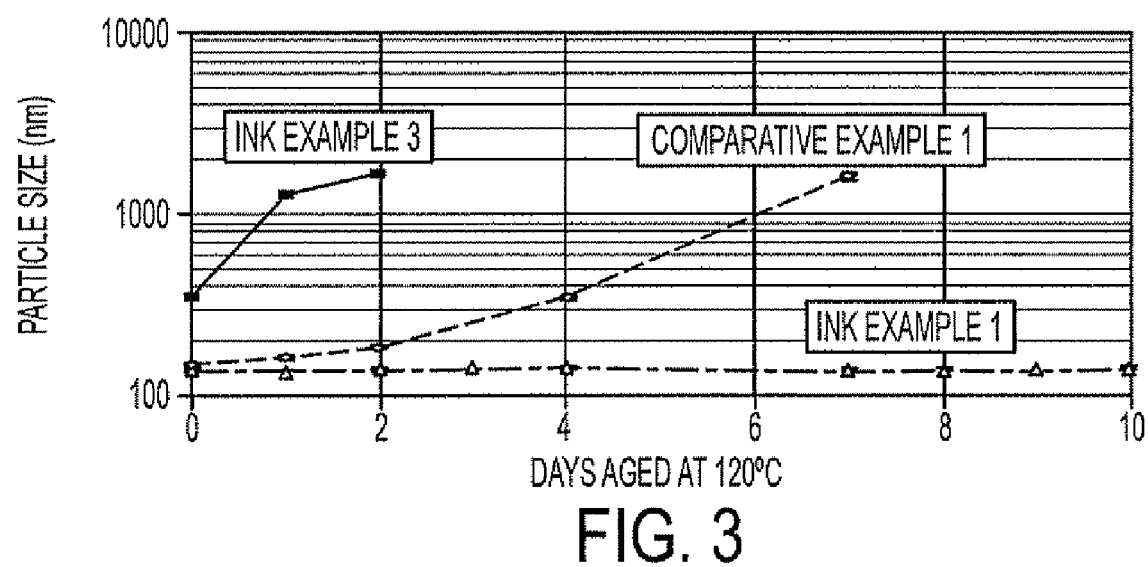
FIG. 3 shows pigment Z-average particle sizes of phase change ink examples 1 and 3 comprising dispersant examples 3 and 1 respectively compared to comparative ink example 1

Again, in a manner similar to the testing described directly above, Example 3 was compared to Comparative Example 1 and Example 1. The results are shown as FIG. 3. As can be seen in the figure, the ink of Example 3 made from a dispersant with a short chain rapidly experienced pigment particle growth (i.e. agglomeration). This indicates that the length of the chain is important to preventing agglomeration.

Figure 4A:
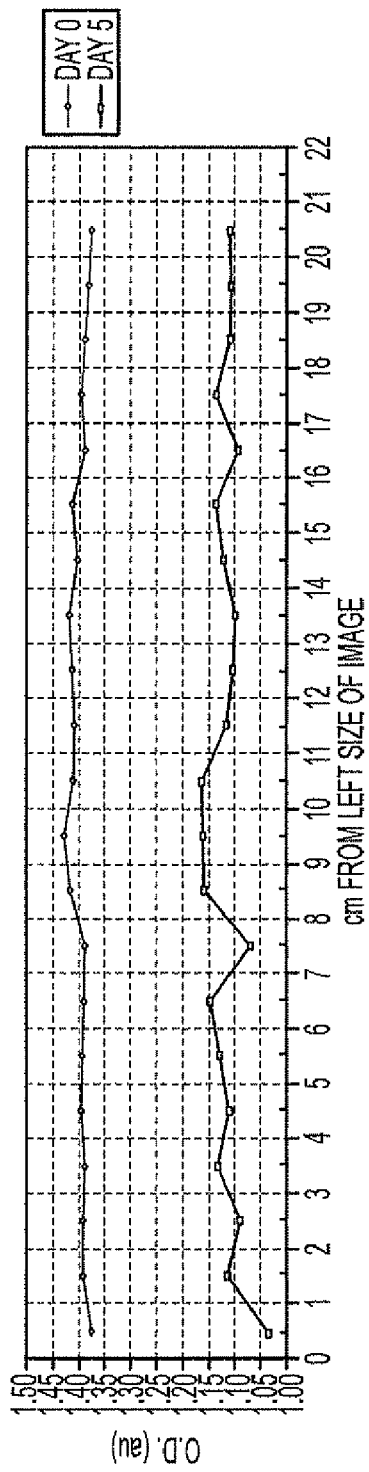
FIG. 4A shows the optical density of prints made from a phase change ink including a dispersant that is a comparative example.
Figure 4B:
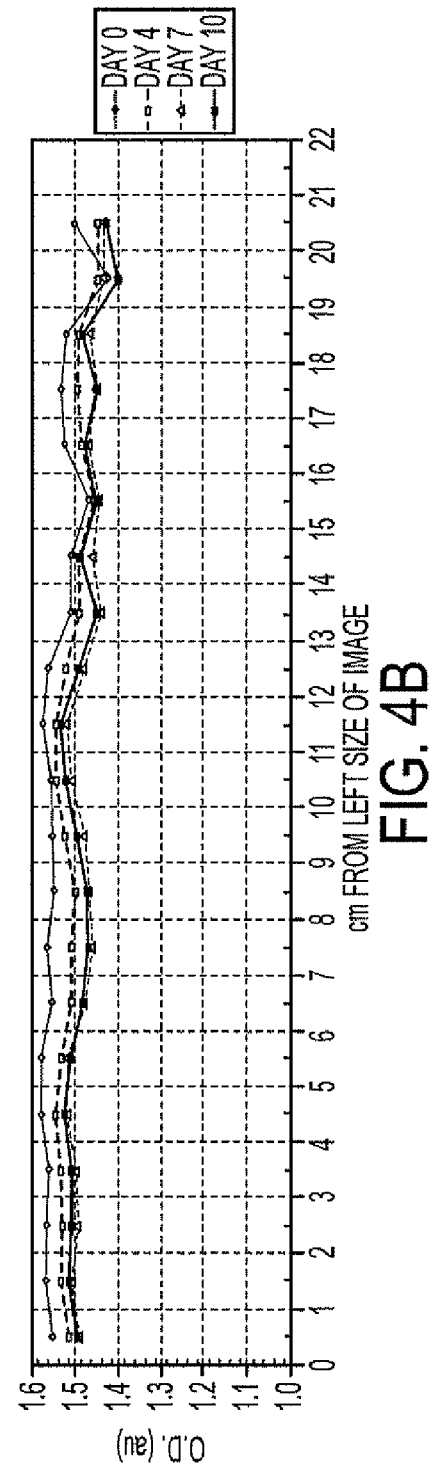
FIG. 4B shows the optical density of prints made from a phase change ink including a dispersant according to this disclosure.

Finally, the stability of the ink as applied by a print head was also tested. Each of the inks of Comparative Example 1 and Example 2 were aged in the printer at 112° C. for up to 10 days, a print was made each day during this time, and the optical density of the print was measured as shown in FIGS. 4A and 4B. Prints made from the ink of Comparative Example 1 exhibited a phenomenon known as banding. Banding is non-uniform jetting that result in a decrease in optical density across the page. As shown in FIG. 4A, optical density of prints made from Comparative Example 1 decreased significantly after aging in the printer for five days. In contrast, as shown in FIG. 4B, the ink according to Example 2 showed no significant change in optical density after aging in the printer for 10 days.

Generally, these results indicate that inks made from the novel dispersant showed stable particle size as determined from both in the oven and in the printer. This indicated that the novel dispersant is capable of stabilizing magenta Pigment Red 57:1 particles in the non-polar ink media under high temperatures. This new dispersant is compatible with the waxy ink vehicle and the quaternary ammonium salt is a strong anchoring group for the pigment magenta 57.1, it is therefore able to stabilize the particles under the high temperatures.

These studies indicate a printable, stable ink that is resistant to agglomeration, aggregation and settling of pigment particles at elevated temperature such as at 120° C.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A chemical compound of the formula:

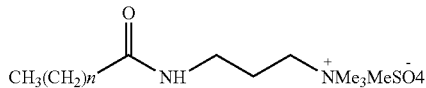

wherein n has a value of from 34 to 52.

2. The chemical compound according to claim 1, wherein n has a value of 36.

3. The chemical compound according to claim 1, wherein n has a value of 46.

4. The chemical compound according to claim 1, wherein the chemical compound has a temperature of onset of crystallization of greater than 90° C. and a peak melting temperature of greater than 100° C.

* * * * *